(12) United States Patent
Grimbergen et al.

(10) Patent No.: US 9,743,997 B2
(45) Date of Patent: Aug. 29, 2017

(54) MAMMOGRAPHY APPARATUS, PADDLE AND METHOD OF MEASURING A CONTACT AREA BETWEEN A BREAST AND THE MAMMOGRAPHY APPARATUS

(71) Applicant: Academisch Medisch Centrum bij de Universiteit van Amsterdam, Amsterdam (NL)

(72) Inventors: Cornelis Antonius Grimbergen, Amsterdam (NL); Gerard Johan Den Heeten, Amsterdam (NL)

(73) Assignee: Academisch Medisch Centrum bij de Universiteit van Amsterdam, Amsterdam (NL)

( * ) Notice: Subject to any disclaimer, the term of this patent is extended or adjusted under 35 U.S.C. 154(b) by 387 days.

(21) Appl. No.: 14/447,088

(22) Filed: Jul. 30, 2014

(65) Prior Publication Data

US 2014/0341338 A1    Nov. 20, 2014

Related U.S. Application Data

(63) Continuation of application No. PCT/NL2013/050089, filed on Feb. 15, 2013.

(30) Foreign Application Priority Data

Feb. 28, 2012   (NL) .................................... 2008377

(51) Int. Cl.
*A61B 6/04*    (2006.01)
*H05G 1/02*    (2006.01)
(Continued)

(52) U.S. Cl.
CPC ............ *A61B 90/17* (2016.02); *A61B 6/0414* (2013.01); *A61B 6/502* (2013.01); *A61B 90/03* (2016.02);
(Continued)

(58) Field of Classification Search
CPC ........... A61B 6/00; A61B 6/04; A61B 6/0407; A61B 6/0414; A61B 6/0442; A61B 6/10;
(Continued)

(56) References Cited

U.S. PATENT DOCUMENTS

2007/0121782 A1   5/2007   Sendai
2008/0043904 A1   2/2008   Hoernig
(Continued)

FOREIGN PATENT DOCUMENTS

WO   2011/102713   8/2011
WO   2013/129920   9/2013

*Primary Examiner* — Anastasia Midkiff
(74) *Attorney, Agent, or Firm* — Peacock Myers, P.C.; Jeffrey D. Myers

(57) ABSTRACT

A mammography apparatus is provided for detecting malignant cells in a breast, comprising an x-ray source and an x-ray detector that cooperates with the x-ray source for providing an x-ray image of said breast, and further comprising a paddle for flattening the breast by pressing it against said x-ray detector, and comprising a contact area measuring device for measuring a contact area between the breast and the paddle, wherein the contact area measuring device is embodied with at least a first laminate of an electrically insulating material and an electrically low resistance material, which first laminate is provided on a side of the paddle facing the breast, and wherein the electrically low resistance material is sandwiched between the paddle and the insulating material.

18 Claims, 2 Drawing Sheets

(51) Int. Cl.
*A61B 90/17* (2016.01)
*A61B 90/00* (2016.01)
*A61B 6/00* (2006.01)

(52) U.S. Cl.
CPC ... *A61B 2090/033* (2016.02); *A61B 2090/034* (2016.02); *A61B 2090/036* (2016.02); *A61B 2560/0406* (2013.01); *A61B 2562/164* (2013.01); *A61B 2576/02* (2013.01); *H05G 1/02* (2013.01)

(58) Field of Classification Search
CPC .. A61B 6/40; A61B 6/50; A61B 6/502; A61B 50/00; A61B 2560/00; A61B 2560/02; A61B 2560/0266; A61B 2560/04; A61B 2560/0406; A61B 2562/00; A61B 2562/16; A61B 2562/164; A61B 2576/00; A61B 2576/02; A61B 90/00; A61B 90/03; A61B 90/033; A61B 90/034; A61B 90/036; A61B 90/06; A61B 90/064; A61B 90/065; A61B 90/17; H05G 1/00; H05G 1/02; H05G 1/26; H05G 1/30
See application file for complete search history.

(56) References Cited

U.S. PATENT DOCUMENTS

| | | | |
|---|---|---|---|
| 2008/0240346 A1 | 10/2008 | Kashiwagi et al. | |
| 2012/0020455 A1* | 1/2012 | Fischer | A61B 6/025 378/37 |
| 2013/0028373 A1* | 1/2013 | Den Heeten | A61B 6/0414 378/37 |
| 2014/0328458 A1* | 11/2014 | Erhard | A61B 6/0414 378/37 |

* cited by examiner

MAMMOGRAPHY APPARATUS, PADDLE AND METHOD OF MEASURING A CONTACT AREA BETWEEN A BREAST AND THE MAMMOGRAPHY APPARATUS

CROSS-REFERENCE TO RELATED APPLICATIONS

This application is a continuation application of Patent Cooperation Treaty Application No. PCT/NL2013/050089, entitled "Mammography Apparatus, Paddle and Method of Measuring a Contact Area Between a Breast and the Mammography Apparatus", filed on Feb. 15, 2013, which claims priority to Netherlands Patent Application No. 2008377, filed on Feb. 28, 2012, and the specifications and claims thereof are incorporated herein by reference.

BACKGROUND OF THE INVENTION

Field of the Invention (Technical Field)

The present invention relates to a mammography apparatus for detecting malignant cells in a breast, which apparatus comprises an x-ray source and an x-ray detector that cooperates with the x-ray source for providing an x-ray image of said breast, and further comprises a paddle for flattening the breast by pressing it against said x-ray detector.

Description of Related Art

A mammography apparatus is known from WO2011/102713 and comprises a contact area measuring device for measuring a contact area between the breast and the paddle.

According to WO2011/102713 the contact area measuring device can be used in a dual fashion. In an embodiment in which the force that is applied to the breast is measured, this force together with the contact area provides an estimation of the average pressure that is applied to the breast. This average pressure can then be controlled at a pre-established level so as to avoid unnecessary and avoidable pain during imaging.

Further, the measured contact area between the breast and the paddle resulting from the breast compression can be used together with the pre-established force level, to calculate and apply a specific mean compression pressure independent of the dimensions of the individual breast. Knowing and controlling this specific mean compression pressure leads to a better standardization of the mammography operation, with improved accuracy of screening whilst avoiding unnecessary pain for the persons being screened.

For the above purposes it is important to reliably measure the contact area between the breast and the paddle.

BRIEF SUMMARY OF THE INVENTION

It is an object of the invention to provide a reliable and accurate measurement of the contact area between the breast and the paddle, and in general to provide an alternative to existing means and methods to provide this measurement.

The invention is embodied in the mammography apparatus, the paddle and the method of measuring the contact area between the breast and paddle as specified in the appended claims.

Further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE SEVERAL VIEWS OF THE DRAWINGS

The accompanying drawings, which are incorporated into and form a part of the specification, illustrate one or more embodiments of the present invention and, together with the description, serve to explain the principles of the invention. The drawings are only for the purpose of illustrating one or more preferred embodiments of the invention and are not to be construed as limiting the invention. In the drawings.

DETAILED DESCRIPTION OF THE INVENTION

Figure 1:
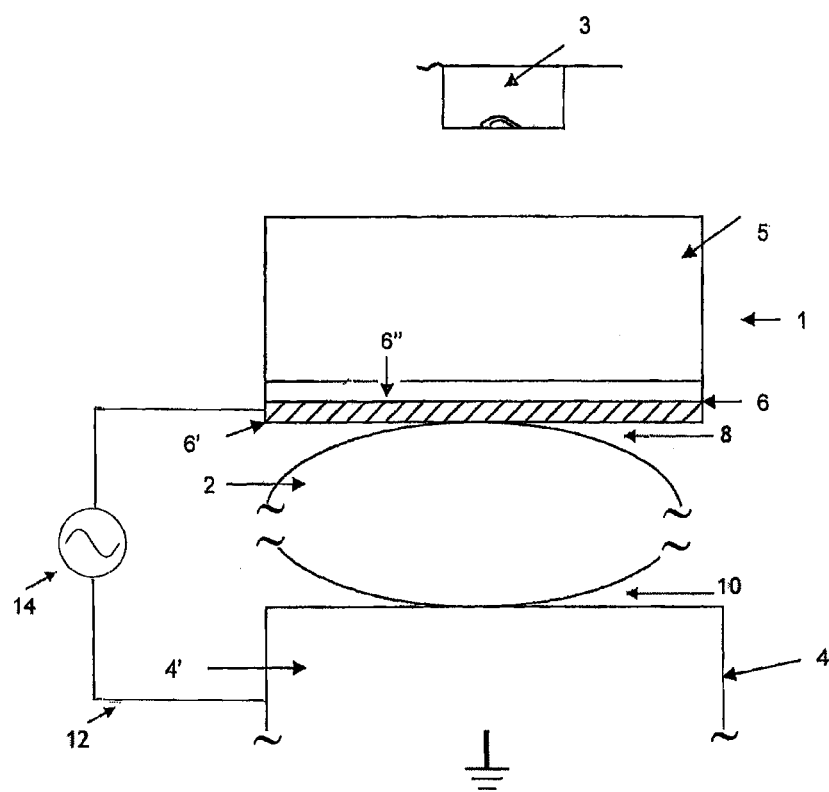
FIG. 1 shows a first embodiment of the mammography apparatus of the invention wherein only the paddle is provided with a laminate.

A first aspect of the invention is that the contact area measuring device is embodied with at least a first laminate of an electrically insulating material and an electrically low resistance material, which first laminate is provided on a side of the paddle facing the breast, wherein the electrically low resistance material is sandwiched between the paddle and the insulating material. This opens the way to carry out an electrical measurement of the actual area at which the breast and paddle are in contact with each other.

According to the invention the measuring of the contact area between the breast and the paddle of the mammography apparatus that further comprises an x-ray detector with a cover, is then carried out such that the electrically conducting x-ray detector cover and the electrically low resistance material of the first laminate are connected to a measurement circuit which is powered by an alternating current excitation source, and that the electrical potential is measured between the x-ray detector and the electrically low resistance material of the first laminate on the paddle, and that said electrical potential is used as a measure for the contact area between the breast and the paddle. This measurement of the contact area will then be based on the change of capacitance between the x-ray detector cover and the electrically low resistance material of the first laminate on the paddle, determined by the breast placed between the paddle and the x-ray detector cover.

It may be beneficial that the contact area measuring device comprises further a second laminate of an electrically low resistance material sandwiched between two layers of an electrically insulating material, which second laminate is provided on a side of the x-ray detector cover facing the breast with one of the layers of insulating material provided against the x-ray detector cover. In this manner both the upper and lower contact areas with the paddle and the x-ray detector cover, respectively can be measured. This is however not a requirement, one can do also with only the first laminate provided on the paddle.

It is possible that the second laminate for application on the x-ray detector cover comprises a layer of an electrically low resistance material and only one layer of an electrically insulating material, and that a separate electrically insulating material is applied between the laminate and the x-ray detector cover. Within the terms of this application both embodiments are considered to constitute a second laminate of an electrically low resistance material sandwiched between two layers of an electrically insulating material.

If such a second laminate is provided on the side of the x-ray detector cover facing the breast, the measurement of the contact areas between the breast and both the paddle and the x-ray detector cover respectively is then preferably carried out by connecting the x-ray detector cover and the electrically low resistance materials of the first and second laminates on the paddle and on the x-ray detector cover to a measurement circuit which is powered by an alternating current excitation source, and that with reference to the potential of the x-ray detector cover the electrical potentials of the electrically low resistance materials of the first and second laminates on the paddle and on the x-ray detector cover are measured, which electrical potentials are then used as measures for the contact areas between the breast and the paddle and the breast and the x-ray detector cover, respectively.

Also the measurement of the contact area between the breast and the x-ray detector cover will then be based on the change of capacitance between the x-ray detector cover and the electrically low resistance material of the second laminate on the x-ray detector cover, as this is determined by the breast placed between the paddle and the x-ray detector cover.

In all embodiments the first laminate on the paddle and—if it is applied—the second laminate on the x-ray detector cover are preferably homogenous and substantially x-ray transparent.

The invention is also embodied in the loose paddle which may be used in a mammography apparatus. The paddle of the invention is provided with a laminate of an electrically insulating material and an electrically low resistance material, and the electrically low resistance material is sandwiched between the paddle and the insulating material. This loose paddle makes retrofit of an existing mammography apparatus into a mammography apparatus according to the invention very easy.

Desirably the first laminate is bendable so as to accommodate to the shape of the paddle. This supports maintaining the accuracy of the measurement, particularly while in practice the shape of the paddle will vary due to the pressure applied to the breast.

Desirably further the electrically low resistance material of the first laminate is attachable to the paddle, preferably by gluing. By ensuring that the position of the laminate on the paddle is invariable, the accuracy of the contact area measurement is prevented from being compromised.

The first and/or second laminates on the paddle and the x-ray detector cover preferably comprise materials with a low level of distortion or damping of the x-rays that are required for imaging the breast. At the same time the laminate on the paddle is preferably optically transparent. On the other hand the insulating material of the laminates must suit the purpose of enabling the capacitance measurement according to the method of the invention. Suitably therefore both objectives can be met when the insulating material of the first and/or second laminate is a thermoplastic having a relative dielectric constant of at least 1.8. Appropriately the insulating material of the first and/or second laminate is then selected from the group comprising polyethylene, cyanoacrylate, polycarbonate. The dielectric constants of these details are 2 (polyethylene); 3 (cyanoacrylate); and 4.4 (polycarbonate). When using a second laminate on the x-ray detector cover, this laminate must be insulated from the conducting x-ray detector cover. For this purpose the laminate is preferably completed with an electrically insulating material on the side which will be provided to the detector cover. In this construction the electrically low resistance material of the second laminate is sandwiched between two insulating layers.

A further aspect is that the epidermis of the breast skin has insulating properties that distort the measurement of the contact area between the breast and the paddle. It has been found advantageous to restrict the influence of these distorting insulating properties of the epidermis by arranging that the insulating material of the first and/or second laminate has a thickness in the range 0.1-0.25 millimeters, preferably approximately 0.17 mm.

For a proper operation of the measurement of the contact area between the breast and the paddle, desirably further the electrically low resistance material of the first and/or second laminate has a specific resistivity of less than $5\times10^{-6}$ Ohm·m.

Suitably the electrically low resistance material of the first and/or second laminate is selected from the group comprising an electron-doped semiconductor and graphene.

If one uses a semiconductor it is preferable that the electrically low resistance material of the first and/or second laminate is indium-doped tin oxide (ITO). This tin oxide layer preferably has a thickness of less than 1 μm.

The invention will hereinafter be further elucidated with reference to the drawing providing schematic figures of two possible embodiments of the mammography apparatus according to the invention, which are not limiting to the appended claims. Whenever in the figures the same reference numerals are applied, these numerals refer to the same parts.

Figure 2:
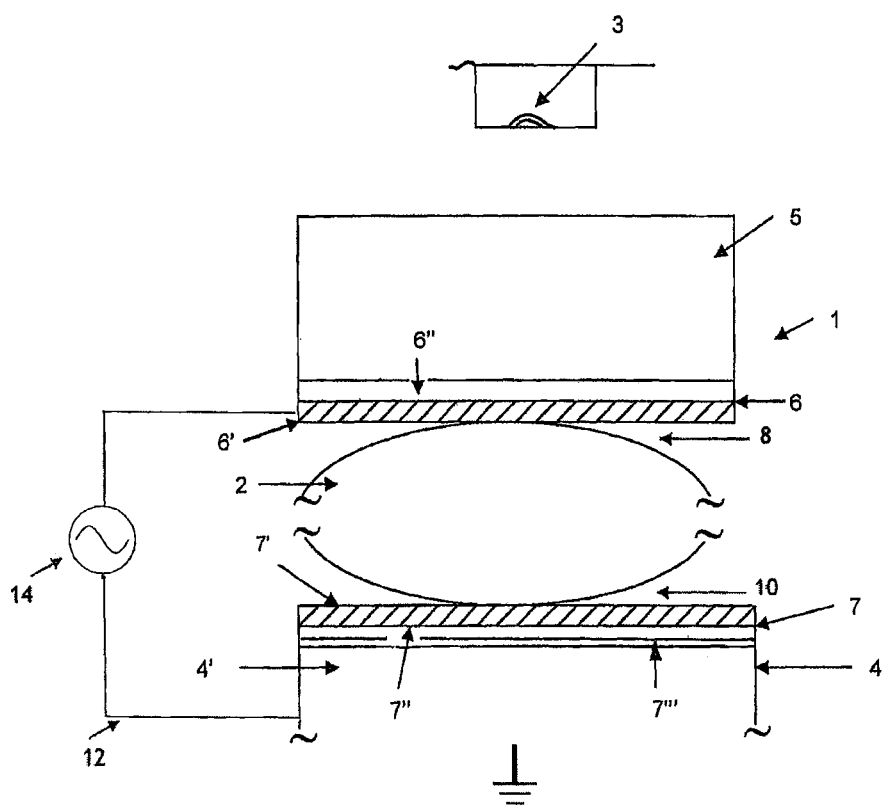
FIG. 2 shows a second embodiment of the mammography apparatus of the invention wherein both the paddle and the x-ray detector are provided with a laminate.

Both FIG. 1 and FIG. 2 provide a schematic view at the mammography apparatus 1 of the invention, which is used for detecting malignant cells in a breast 2.

The mammography apparatus 1 comprises in known way an x-ray source 3 and an x-ray detector 4' that cooperates with the x-ray source 3 for providing an x-ray image of the breast 2. The apparatus further has a paddle 5 for flattening the breast 2 by pressing the breast against the x-ray detector cover 4.

According to the invention there is a contact area measuring device for measuring a contact area between the breast and the paddle 8, which is embodied with at least a first laminate 6 of an electrically insulating material 6' and an electrically low resistance material 6".

FIG. 1 shows that the first laminate 6 is provided on a side of the paddle 5 facing the breast 2, while the electrically low resistance material 6" is sandwiched between the paddle 5 and the insulating material 6'. It is desirable that the first laminate 6 is bendable so as to accommodate to the shape of the paddle 5, and that the electrically low resistance material 6" of the first laminate 6 is attachable to the paddle 5, preferably by gluing.

FIG. 2 shows another embodiment in which the contact area measuring device comprises a second laminate 7 of an electrically low resistance material 7" sandwiched between two layers 7',7''' of electrically insulating materials, which second laminate 7 is provided on a side of the x-ray detector cover 4 facing the breast 2. Also here the insulating material 7' ensures isolation of the breast 2 from the electrically low resistance material 7" of the second laminate 7. In the shown example the laminate 7 is provided on the x-ray detector cover 4 wherein the intermediate insulating material 7''' attached to the x-ray detector cover 4 forms an integral part of the laminate 7. It is however also possible that this latter intermediate insulating material 7'" is applied separately from the laminate 7.

Preferably the insulating material 6',7' of the first laminate 6 and/or second laminate 7 is a thermoplastic having a relative dielectric constant of at least 1.8. The insulating material 6',7' of the first laminate 6 and/or second laminate 7 is preferably selected from the group comprising polyethylene, cyanoacrylate, polycarbonate. Further the insulating material 6',7' of the first laminate 6 and/or second laminate 7 has a thickness in the range 0.1-0.25 millimeters, preferably approximately 0.17 mm.

The electrically low resistance material 6",7" of the first laminate 6 and/or second laminate 7 preferably has a specific resistivity of less than $5 \times 10^{-6}$ Ohm·m, and is selected from the group comprising an electron-doped semiconductor and graphene. When of the semiconductor type, the electrically low resistance material 6",7" is preferably indium-doped tin oxide, having a thickness of less than 1 µm.

The invention is also embodied in the separate paddle 5 for use in a mammography apparatus 1 according to the invention and is provided with a laminate 6 of an electrically insulating material 6' and an electrically low resistance material 6", wherein the electrically low resistance material 6" is sandwiched between the paddle 5 and the insulating material 6'.

When using the paddle 5 of the mammography apparatus 1 as shown in FIG. 1 in a method for measuring the contact area between breast and paddle 8, wherein the mammography apparatus 1 further comprises an x-ray detector cover 4, the x-ray detector cover 4 and the electrically low resistance material 6" of the first laminate 6 are connected to a measurement circuit 12 which is powered by an alternating current excitation source 14. The electrical potential is then measured between the x-ray detector cover 4 which is grounded, and the electrically low resistance material 6" of the first laminate 6 on the paddle 5, and this electrical potential is according to the invention used as a measure for the contact area between the breast and the paddle 8. This is done by calculating the changed electrical capacitance as determined by the placement of the breast between the paddle and the x-ray detector cover.

An alternative relates to the use of the mammography apparatus 1 that is shown in FIG. 2. The contact area between the breast and the paddle 8, and between the breast and the x-ray detector cover 10, is then measured by connecting x-ray detector cover 4 and the electrically low resistance materials 6", 7" of the first laminate 6 and the second laminate 7 on the paddle 5 and on the x-ray detector cover 4, respectively, to a measurement circuit 12 which is powered by an alternating current excitation source 14. Then with reference to the potential of the x-ray detector cover 4, the electrical potentials are measured of the electrically low resistance materials 6", 7" of the first laminate 6 on the paddle and the second laminate 7 on the x-ray detector cover 4, and these electrical potentials are used as a measure for the contact areas between the breast and the paddle 8 and the breast and the x-ray detector cover 10, respectively.

The way in which the measurement circuit 12 can be implemented can be in the form of applying voltage dividers or by measuring the time it takes to fully charge the capacitance between the low electrical resistivity material 6" of the laminate 6 that is provided on the paddle 5 and the x-ray detector cover 4 (and between the low electrical resistivity material 7" and the x-ray detector cover 4 when the detector 4' is provided with a laminate 7). The way this can be implemented is known to the person skilled in the art and requires no further elucidation with reference to the drawing.

It is explicitly remarked that the above elucidation of the features of the invention are not intended to limit the appended claims to the specific examples that are provided herewith. On the contrary, the invention is solely defined by the appended claims and the above elucidation merely serves to elucidate the claims if any ambiguity would reside in these claims. Without departing from the scope of the claims many variations are therefore feasible.

What is claimed is:

1. A mammography apparatus for detecting malignant cells in a breast comprising an x-ray source and an x-ray detector that cooperates with the x-ray source for providing an x-ray image of said breast, and further comprising a paddle for flattening the breast by pressing it against an x-ray detector cover, and comprising a contact area measuring device for measuring a contact area between the breast and the paddle, wherein the contact area measuring device is embodied with at least a first laminate of an electrically insulating material and an electrically low resistance material, which first laminate is provided on a side of the paddle facing the breast, wherein the electrically low resistance material is sandwiched between the paddle and the insulating material.

2. The mammography apparatus according to claim 1, wherein the contact area measuring device comprises further a second laminate of an electrically low resistance material sandwiched between two layers of an electrically insulating material, which second laminate is provided on a side of the x-ray detector cover facing the breast with one of the layers of insulating material provided against the x-ray detector cover.

3. The mammography apparatus according to claim 2, wherein the first laminate and/or the second laminate are homogenous and substantially x-ray transparent.

4. The mammography apparatus according to claim 1, wherein the first laminate is optically transparent.

5. The mammography apparatus according to claim 1, wherein the first laminate is bendable so as to accommodate to the shape of the paddle.

6. The mammography apparatus according to claim 1, wherein the electrically low resistance material of the first laminate is attachable to the paddle.

7. The mammography apparatus according to claim 2, wherein the insulating material of the first laminate and/or second laminate is a thermoplastic having a relative dielectric constant of at least 1.8.

8. The mammography apparatus according to claim 2, wherein the insulating material of the first laminate and/or second selected from the group comprising polyethylene, cyanoacrylate, and polycarbonate.

9. The mammography apparatus according to claim 2, wherein the insulating material of the first laminate and/or second laminate has a thickness in the range 0.1-0.25 millimeters.

10. The mammography apparatus according to claim 2, wherein the electrically low resistance material of the first laminate and/or second laminate has a specific resistivity of less than $5 \times 10^{-6}$ Ohm·m.

11. The mammography apparatus according to claim 2, wherein the electrically low resistance material of the first laminate and/or second laminate is selected from the group comprising an electron-doped semiconductor and graphene.

12. The mammography apparatus according to claim 2, wherein the electrically low resistance material of the first laminate and/or second laminate is indium-doped tin oxide.

13. The mammography apparatus according to claim 12, wherein the indium-doped tin oxide has a thickness of less than 1 μm.

14. A paddle for use in a mammography apparatus according to claim 1, wherein said paddle is provided with a laminate of an electrically insulating material and an electrically low resistance material, wherein the electrically low resistance material is sandwiched between the paddle and the insulating material.

15. A method for measuring a contact area between a breast and a paddle of a mammography apparatus that further comprises an x-ray detector with a x-ray detector cover, wherein a first laminate of an electrically insulating material and an electrically low resistance material is provided on a side of the paddle facing the breast, and wherein the electrically low resistance material is sandwiched between the paddle and the insulating material, wherein the x-ray detector cover and the electrically low resistance material of the first laminate are connected to a measurement circuit which is powered by an alternating current excitation source, and that the electrical potential is measured between the x-ray detector cover and the electrically low resistance material of the first laminate on the paddle, and wherein said electrical potential is used as a measure for the contact area between the breast and the paddle.

16. The method according to claim 15, wherein a second laminate of an electrically low resistance material sandwiched between two layers of an electrically insulating material is provided on the side of the x-ray detector cover facing the breast, and that the x-ray detector cover and the electrically low resistance materials of the first and second laminates of the paddle and the x-ray detector cover are connected to a measurement circuit which is powered by an alternating current excitation source, wherein with reference to the potential of the x-ray detector cover the electrical potentials are measured of the electrically low resistance materials of the first and second laminates on the paddle and the x-ray detector cover, and wherein said electrical potentials are used as measures for contact areas between the breast and the paddle and the breast and the x-ray detector cover, respectively.

17. The mammography apparatus according to claim 6, wherein the electrically low resistance material of the first laminate is attachable to the paddle by gluing.

18. The mammography apparatus according to claim 9, wherein the insulating material of the first laminate and/or second laminate has a thickness of approximately 0.17 millimeters.

* * * * *